US010759731B2

(12) United States Patent
Itatani et al.

(10) Patent No.: US 10,759,731 B2
(45) Date of Patent: Sep. 1, 2020

(54) METHOD FOR PRODUCING C2-C20 FLUORINE-CONTAINING ORGANIC ACID, AND COMPOSITION COMPRISING C2-C20 FLUORINE-CONTAINING ORGANIC ACID

(71) Applicant: DAIKIN INDUSTRIES, LTD., Osaka-shi, Osaka (JP)

(72) Inventors: Shuuji Itatani, Osaka (JP); Mihoko Ohashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/309,497

(22) PCT Filed: Jun. 9, 2017

(86) PCT No.: PCT/JP2017/021478
§ 371 (c)(1),
(2) Date: Dec. 13, 2018

(87) PCT Pub. No.: WO2017/217333
PCT Pub. Date: Dec. 21, 2017

(65) Prior Publication Data
US 2019/0330135 A1    Oct. 31, 2019

(30) Foreign Application Priority Data

Jun. 16, 2016  (JP) ................................ 2016-119807

(51) Int. Cl.
| | |
|---|---|
| *C07C 53/21* | (2006.01) |
| *C07C 51/363* | (2006.01) |
| *C07C 51/44* | (2006.01) |
| *C07C 303/22* | (2006.01) |
| *C07C 303/44* | (2006.01) |
| *C07C 303/06* | (2006.01) |
| *C07C 309/06* | (2006.01) |

(52) U.S. Cl.
CPC ............ *C07C 53/21* (2013.01); *C07C 51/363* (2013.01); *C07C 51/44* (2013.01); *C07C 303/22* (2013.01); *C07C 303/44* (2013.01); *C07C 309/06* (2013.01)

(58) Field of Classification Search
CPC ....... C07C 53/21; C07C 51/363; C07C 51/44; C07C 303/44; C07C 309/06; C07C 303/22; C07C 51/48
See application file for complete search history.

(56) References Cited

U.S. PATENT DOCUMENTS

| | | | | |
|---|---|---|---|---|
| 4,282,162 | A | * 8/1981 | Kuhls | .................... C07C 51/47 554/185 |
| 5,312,935 | A | 5/1994 | Mayer et al. | |

FOREIGN PATENT DOCUMENTS

| | | |
|---|---|---|
| JP | 2007-099624 A | 4/2007 |
| JP | 2010-065034 A | 3/2010 |
| WO | 2010/027103 A1 | 3/2010 |

OTHER PUBLICATIONS

Wikipedia, Sulfuric Acid, 2019, recovered from https://en.wikipedia.org/wiki/Sulfuric_acid on Oct. 23, 2019, pp. 1-18. (Year: 2019).*
International Search Report for PCT/JP2017/021478 dated Jul. 11, 2017 [PCT/ISA/210].
International Preliminary Report on Patentability with the translation of Written Opinion dated Dec. 27, 2018 issued by the International Bureau in PCT/JP2017/021478.
Communication dated Jan. 14, 2020 from European Patent Office in EP Application No. 17813230.4.

* cited by examiner

*Primary Examiner* — Paul A Zucker
(74) *Attorney, Agent, or Firm* — Sughrue Mion, PLLC

(57) ABSTRACT

There is provided a method for producing a $C_2$-$C_{20}$ fluorine-containing organic acid with reduced fluorine-free organic compound. A method for producing a $C_2$-$C_{20}$ fluorine-containing organic acid, the method including contacting a mixture containing a $C_2$-$C_{20}$ fluorine-containing organic acid and a fluorine-free organic compound with a concentrated sulfuric acid and then separating a $C_2$-$C_{20}$ fluorine-containing organic acid phase from a concentrated sulfuric acid phase. The contacting is conducted such that an amount of water present in the concentrated sulfuric acid phase is 10% by mass or less, and the $C_2$-$C_{20}$ fluorine-containing organic acid is obtained in the form of the $C_2$-$C_{20}$ fluorinated organic acid phase having a reduced content ratio of the fluorine-free organic compound compared with said mixture.

20 Claims, 2 Drawing Sheets

METHOD FOR PRODUCING C2-C20 FLUORINE-CONTAINING ORGANIC ACID, AND COMPOSITION COMPRISING C2-C20 FLUORINE-CONTAINING ORGANIC ACID

CROSS REFERENCE TO RELATED APPLICATIONS

This application is a National Stage of International Application No. PCT/JP2017/021478, filed on Jun. 9, 2017, which claims priority from Japanese Patent Application No. 2016-119807, filed on Jun. 16, 2016.

TECHNICAL FIELD

The present invention relates to a method for producing a C2-C20 fluorine-containing organic acid. Also, the present invention relates to a composition comprising a C2-C20 fluorine-containing organic acid.

BACKGROUND ART

Conventionally, a C2-C20 fluorine-containing organic acid is known and this fluorine-containing organic acid, in particular a C2-C8 fluorine-containing organic acid, is used as an emulsifier, for example, for producing polymers by emulsion polymerization. In an emulsifier, impurities such as water and others may be mixed depending on a production method and/or a manner of use of an emulsifier. In order not to have unintended effect on emulsion polymerization, it is preferable that an amount of impurities in an emulsifier is small. In addition, emulsifiers are relatively expensive, so it is desirable to collect them after use and reuse them.

For example, Patent Literature 1 discloses that a mixture containing a fluorocarboxylic acid, which is one of emulsifiers, and water is dehydrated by contacting it with a concentrated sulfuric acid to obtain a dehydrated fluorocarboxylic acid solution, and then the dehydrated fluorocarboxylic acid solution is purified by distillation operation.

CITATION LIST

Patent Literature

Patent Literature 1: JP 2010-65034 A

SUMMARY OF INVENTION

Technical Problem

The present inventors have been focused on that, in some cases, a fluorine-free (or fluorine-non-containing) organic compound is mixed as an impurity in a C2-C20 fluorine-containing organic acid. Such a fluorine-free organic compound includes, for example, fluorine-free carboxylic acids, hydrocarbons, polyethers and the like which can be used as dispersion stabilizers (stabilizing aids) in emulsion polymerization or for other purposes.

Since such a fluorine-free organic compound is usually present as a trace component in a C2-C20 fluorine-containing organic acid, it is difficult to separate by distillation operation. If a fluorine-free organic compound can be effectively removed from a C2-C20 fluorine-containing organic acid, it is convenient, for example, because it can regenerate the spent C2-C20 fluorine-containing organic acid as an emulsifier and reuse it as an emulsifier.

An object of the present invention is to provide a method which is possible to effectively remove a fluorine-free organic compound from a mixture containing a C2-C20 fluorine-containing organic acid and a fluorine-free organic compound, in other words, to provide a method for producing a C2-C20 fluorine-containing organic acid with reduced fluorine-free organic compound. A further object of the present invention is to provide a novel composition, which can be obtained by such a method, comprising a C2-C20 fluorine-containing organic acid.

Solution to Problem

Conventionally, in post-treatment or regeneration treatment of the fluorocarboxylic acid which is one of emulsifiers, a concentrated sulfuric acid has been used for dehydrating from a mixture containing fluorocarboxylic acid and water (see Patent Literature 1). After contacting and mixing a mixture containing fluorocarboxylic acid and water with a concentrated sulfuric acid, it has been separated into an organic phase and an aqueous phase to obtain fluorocarboxylic acid in the form of the organic phase. If it is assumed that an organic compound is mixed as an impurity in such a contacting and mixing system containing fluorocarboxylic acid, water and a concentrated sulfuric acid, it is generally considered that the organic compound is distributed to the organic phase rather than the aqueous phase.

However, the present inventors have obtained unique knowledge that a fluorine-free organic compound can be extracted from a C2-C20 fluorine-containing organic acid phase into a concentrated sulfuric acid phase (or at least partially removed from a C2-C20 fluorine-containing organic acid) by contacting a mixture containing a C2-C20 fluorine-containing organic acid and a fluorine-free organic compound with a concentrated sulfuric acid in a state in which substantially no water or a very small amount of water is present. As a result of further intensive studies, the present inventors have completed the present invention.

According to the first aspect of the present invention, there is provided a method for producing a C2-C20 fluorine-containing organic acid, wherein the method comprises contacting a mixture containing a C2-C20 fluorine-containing organic acid and a fluorine-free organic compound with a concentrated sulfuric acid and then separating a C2-C20 fluorine-containing organic acid phase from a concentrated sulfuric acid phase, wherein the contacting is conducted such that an amount of water present in the concentrated sulfuric acid phase is 10% by mass or less, and the C2-C20 fluorine-containing organic acid is obtained in the form of the C2-C20 fluorinated organic acid phase having a reduced content ratio of the fluorine-free organic compound compared with said mixture.

According to one mode of the present invention, the fluorine-free organic compound may comprise a C1-C50 fluorine-free organic compound, more specifically, may comprise at least one selected from the group consisting of a C1-C50 fluorine-free carboxylic acid and derivative thereof, a C8-C50 fluorine-free hydrocarbon, a C6-C50 fluorine-free phenol, a C1-C30 fluorine-free alcohol, a C8-C50 fluorine-free polyether and a C10-C20 fluorine-free alkyl group-containing ionic compound.

According to one mode of the present invention, the C2-C20 fluorine-containing organic acid may comprise at least one selected from the group consisting of a C2-C20 fluorocarboxylic acid and salts thereof.

According to one mode of the present invention, the mixture containing the C2-C20 fluorine-containing organic acid and the fluorine-free organic compound may be previously (prior to the contacting with the concentrated sulfuric acid, which is carried out with the above condition relating to the amount of water) subjected to dehydration treatment. Such a dehydration treatment may be carried out by washing the mixture containing the C2-C20 fluorine-containing organic acid and the fluorine-free organic compound with a sulfuric acid aqueous solution having a sulfuric acid concentration of 70% by mass or more, but is not limited thereto.

According to another aspect of the present invention, there is provided a composition (hereinafter simply referred to as the composition of the present invention) comprising a C2-C20 fluorine-containing organic acid and a fluorine-free organic compound, wherein a content of the fluorine-free organic compound in the composition is 0.001 to 0.1 ppm by mass.

In the composition of the present invention, the C2-C20 fluorine-containing organic acid and the fluorine-free organic compound may be the same as those described above with respect to the method for producing a C2-C20 fluorine-containing organic acid of the present invention.

According to one mode of the present invention, a content of water in the composition of the present invention may be 0.1% by mass or less.

Advantageous Effects of Invention

According to the present invention, in the case of contacting a mixture containing a C2-C20 fluorine-containing organic acid and a fluorine-free organic compound with a concentrated sulfuric acid and then separating a C2-C20 fluorine-containing organic acid phase from a concentrated sulfuric acid phase, this contacting is conducted such that an amount of water present in the concentrated sulfuric acid phase is 10% by mass or less and thus the C2-C20 fluorine-containing organic acid can be obtained in the form of the C2-C20 fluorinated organic acid phase having a reduced content ratio of a fluorine-free organic compound compared with said mixture. Thereby, there is provided a method for producing a C2-C20 fluorine-containing organic acid with reduced fluorine-free organic compound. Further, according to the present invention, there is provided a novel composition comprising a C2-C20 fluorine-containing organic acid and a fluorine-free organic compound, wherein a content of a fluorine-free organic compound in the composition is 0.001 to 0.1 ppm by mass. Such a composition of the present invention can be obtained by the method for producing a C2-C20 fluorine-containing organic acid of the present invention, but is not limited thereto.

DESCRIPTION OF EMBODIMENTS

Figure 1A:
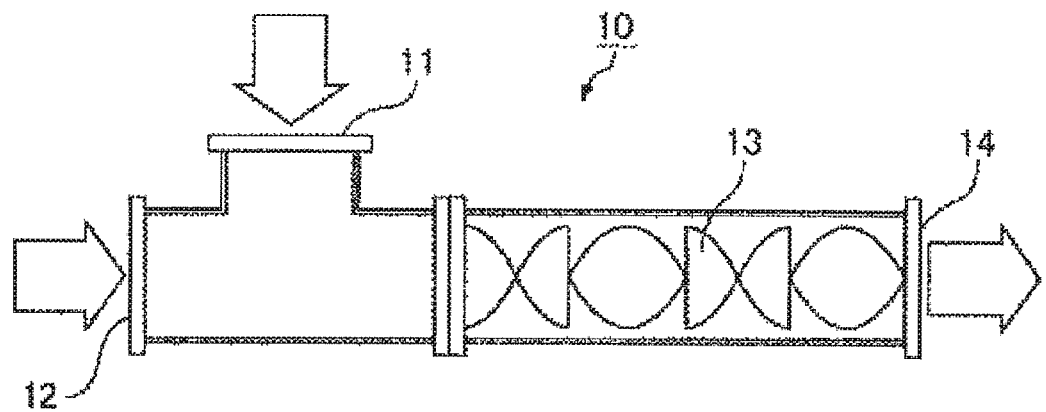
FIG. 1 (a) is a schematic sectional view showing a configuration of a static mixer, and FIG. 1 (b) is a schematic view showing a configuration of a liquid-liquid separation column.

Regarding the method for producing a C2-C20 fluorine-containing organic acid and the composition containing a C2-C20 fluorine-containing organic acid of the present invention, it will be described in detail below through embodiments of the present invention. However, the present invention is not limited to these embodiments.

First, a mixture containing a C2-C20 fluorine-containing organic acid and a fluorine-free organic compound used in this embodiment is prepared.

The C2-C20 fluorine-containing organic acid may be an organic acid having 2 to 20 carbon atoms and fluorine. Examples of the C2-C20 fluorine-containing organic acid include C2-C20 fluorine-containing carboxylic acids and salts thereof, and C2-C20 fluorine-containing sulfonic acids and salts thereof.

Examples of the C2-C20 fluorine-containing carboxylic acid can include the compound represented by the formula (i):

X—Rf—COOH (i)

wherein X is H, F or Cl, Rf is a linear or branched C1-C19 fluoroalkylene group, a C1-C19 group having a monooxyfluoroalkylene group or a C1-C19 group having a polyoxyfluoroalkylene group.

The linear or branched C1-C19 fluoroalkylene group in the above-mentioned Rf group may be $C_aF_bH_{2a-b}$ (wherein a is an integer of 1 to 19 and b is an integer of 2a or less). Examples of such a group can include $CF_2$, $C_2F_4$, $C_3F_6$, $C_4F_8$, $C_5F_{12}$, $C_6F_{12}$, $C_7F_{14}$, CHF, $C_2F_3H$, $C_2F_2H_2$, $C_2FH_3$, $C_3F_5H$, $C_3F_4H_2$, $C_3F_3H_3$, $C_3F_2H_4$, $C_3F_1H_5$, $C_4F_7H$, $C_4F_6H_2$, $C_4F_5H_3$, $C_4F_4H_4$, $C_4F_3H_5$, $C_4F_2H_6$, $C_4FH_7$, $C_5F_9H$, $C_5F_8H_2$, $C_5F_7H_3$, $C_5F_6H_4$, $C_5F_5H_5$, $C_5F_4H_6$, $C_5F_3H_7$, $C_5F_2H_8$, $C_5FH_9$, $C_6F_{11}H$, $C_6F_{10}H_2$, $C_6F_9H_3$, $C_6F_8H_4$, $C_6F_7H_5$, $C_6F_6H_6$, $C_6F_5H_7$, $C_6F_4He$, $C_6F_3H_9$, $C_6F_2H_{10}$, $C_6FH_{11}$, $C_7F_{13}H$, $C_7F_{12}H_2$, $C_7F_{11}H_3$, $C_7F_{10}H_4$, $C_7F_9H_5$, $C_7F_8H_6$, $C_7F_7H_7$, $C_7F_6H$, $C_7F_5H$, $C_7F_4H_{10}$, $C_7F_3H_{11}$, $C_7F_2H_{12}$ and $C_7FH_{13}$.

Examples of the C1-C19 group having a monooxyfluoroalkylene group and the C1-C19 group having a polyoxyfluoroalkylene group in the above-mentioned Rf group can include the group represented by the formulae:

$(CF_2)_l$—$(CF_2OCF_2)_m$—$(CF_2OCF(CF_3))_n$      formula (a)

$(CF_2)_l$—$(CHFOCF_2)_m$—$(CF_2OCF(CF_3))_n$      formula (b)

$(CF_2)_l$—$(CF_2OCHF)_m$—$(CF_2OCF(CF_3))_n$      formula (c)

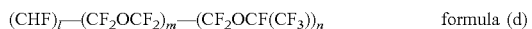

$(CHF)_l$—$(CF_2OCF_2)_m$—$(CF_2OCF(CF_3))_n$      formula (d)

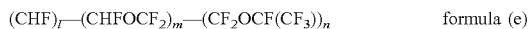

$(CHF)_l$—$(CHFOCF_2)_m$—$(CF_2OCF(CF_3))_n$      formula (e)

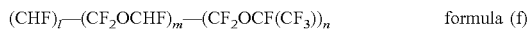

$(CHF)_l$—$(CF_2OCHF)_m$—$(CF_2OCF(CF_3))_n$      formula (f)

wherein l is 0 or an integer of 1 to 17, m is 0 or an integer of 1 to 9 and n is an integer of 0 to 6, provided that l+2m+3n does not exceed 19 and that a case where m and n are 0 is excluded.

Further, in the above formulae, the order of presence of the respective repeating units in parentheses is arbitrary.

In formula (i), more preferably, X is H or F, Rf is a C1-C19 group having a monooxyfluoroalkylene group or a C1-C19 group having a polyoxyfluoroalkylene group, further preferably Rf is a C1-C7 group, particularly a C1-C6 group, each having a monooxyfluoroalkylene group or a C1-C7 group, particularly a C1-C6 group, each having a polyoxyfluoroalkylene group.

Further preferably, the C2-C20 fluorine-containing carboxylic acid is the perfluorocarboxylic acid represented by the formula (i-a):

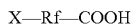

X—Rf—COOH (i-a)

wherein X is H or F, Rf is the group represented by the formula (a)

$$(CF_2)_l\text{—}(CF_2OCF_2)_m\text{—}(CF_2OCF(CF_3))_n \quad \text{formula (a)}$$

wherein, in the above formula (a), l is 0 or an integer of 1 to 17, m is 0 or an integer of 1 to 9 and n is an integer of 0 to 6, provided that l+2m+3n does not exceed 19, that a case where m and n are 0 is excluded and that the order of presence of the respective repeating units in parentheses is arbitrary.

In the above-mentioned fluorine-containing carboxylic acid, the number of carbon atoms is preferably 4 to 10, more preferably 5 to 8, and particularly preferably 6 to 8.

As the C5-C8 fluorine-containing carboxylic acid in a preferred embodiment, for example, it can be exemplified by
$CF_3OCF(CF_3)CF_2OCF(CF_3)$ COOH,
$CF_3CF_2CF_2CF_2OCF_2COOH$,
$CF_3OCF_2CF_2CF_2OCHFCF_2COOH$,
$CF_3CF_2OCF_2CF_2OCF_2COOH$,
$CF_3OCF_2CFCF_2OCHFCF_2COOH$,
$CF_3(CF_2)_4COOH$,
$CF_3CF_2CF_2OCF(CF_3)CCOH$,
$H(CF_2)_6COOH$,
$H(CF_2)_4COOH$,
$CH_2\text{=}CFCF_2OCF(CF_3)COOH$,
$CF_3(CF_2)_6COOH$,
$CF_3CF_2CF_2OCF_2CF_2OCF(CF_3)COOH$
and the like.

Examples of the C2-C20 fluorine-containing sulfonic acid can include perfluoropropanesulfonic acid, perfluorobutanesulfonic acid, perfluorohexanesulfonic acid, $CF_2\text{=}CFOCF_2CF_2SO_3H$, $CF_2\text{=}CFOCF_2CF(CF_3)OCF_2CF_2SO_3H$, $CF_3(CF_2)_8SO_3H$, and the like.

Examples of the salts of the fluorine-containing carboxylic acid and the fluorine-containing sulfonic acid can include a salt having a monovalent cation as a counter ion, for example, alkali metal salts such as potassium salts and sodium salts, ammonium salts and amine salts (for example, alkylamine salts such as methylamine, dimethylamine, trimethylamine, ethylamine, diethylamine and triethylamine etc.), and the like.

The fluorine-free organic compound may be an organic compound containing no fluorine. Examples of the fluorine-free organic compound include a C1-C50 fluorine-free organic compound. Examples of the C1-C50 organic compound include at least one selected from the group consisting of a C1-C50 fluorine-free carboxylic acid and derivative thereof, a C8-C50 fluorine-free hydrocarbon, a C6-C50 fluorine-free phenol, a C1-C30 fluorine-free alcohol, a C8-C50 fluorine-free polyether and a C10-C20 fluorine-free alkyl group-containing ionic compound. The number of carbon atoms of the above organic compounds is preferably in the range of 10 to 40, more preferably in the range of 14 to 35.

The C1-C50 fluorine-free carboxylic acid may have one or more carboxyl groups. Examples of the derivative of the C1-C50 fluorine-free carboxylic acid can include a carboxylic acid ester and/or those having substituents such as a hydroxy group, an alkoxy group and the like. Examples of the C1-C50 fluorine-free carboxylic acid and derivative thereof include the followings:

a C8-C50 fluorine-free aromatic carboxylic acid and ester thereof, for example, phthalic acid, phthalic acid anhydride, phthalimide, phthalate (for example, sodium salt or potassium salt), phthalic acid mono- or di-alkyl ester (for example, dimethyl phthalate, diethyl phthalate, diallyl phthalate, dibutyl phthalate, diisobutyl phthalate, dinormal hexyl phthalate, bis(2-ethylhexyl) phthalate, dinormal octyl phthalate, diisononyl phthalate, dinonyl phthalate, diisodecyl phthalate, bisbutyl benzyl phthalate, etc.), benzoic acid, benzoic acid alkyl ester (for example, methyl benzoate, ethyl benzoate, propyl benzoate, butyl benzoate, etc.), salicylic acid, salicylic acid alkyl ester (for example, methyl salicylate, ethyl salicylate, propyl salicylate, butyl salicylate etc.), gallic acid, gallic acid alkyl ester (for example, methyl gallate, ethyl gallate, propyl gallate, butyl gallate, etc.), melitic acid, melitic acid anhydride, cinnamic acid, cinnamic acid anhydride, cinnamic acid alkyl ester (for example, methyl cinnamate, ethyl cinnamate, propyl cinnamate, butyl cinnamate, etc.);

a C1-C50 fluorine-free aliphatic carboxylic acid and ester thereof, for example, formic acid, methanoic acid, ethanoic acid, propanoic acid, butanoic acid, pentanoic acid, hexanoic acid, heptanoic acid, octanoic acid, nonanoic acid, decanoic acid, dodecanoic acid, tetradecanoic acid, hexadecanoic acid, heptadecanoic acid, octadecanoic acid, oleic acid, linoleic acid, linolenic acid, arachidonic acid, eicosapentaenoic acid, docosahexaenoic acid, $CF_3(CF_2)_6COOH$, $CF_3(CF_2)$ COOH, $H(CF_2)_8COOH$, $H(CF_2)_{10}COOH$, $CF_3CF_2CF_2OCF(CF)$ $CF_2OCF(CF_3)$ COOH, oxalic acid, malonic acid, succinic acid, glutaric acid, adipic acid, 1,2,3-propanetricarboxylic acid etc., and alkyl esters thereof (for example, methyl ester, ethyl ester, propyl ester, butyl ester, etc.), and/or those in which one or more hydrogen atoms are substituted with a hydroxy group, an alkoxy group or the like (for example, citric acid and the like).

The number of carbon atoms of the carboxylic acid and its derivative is preferably in the range of 1 to 30, more preferably in the range of 1 to 20.

Examples of the C8-C50 fluorine-free hydrocarbon include a C8-C50 linear, branched or alicyclic and saturated or unsaturated hydrocarbon. The number of carbon atoms is more preferably from 10 to 40, even more preferably from 20 to 40. A C20-C40 saturated hydrocarbon is sometimes referred to as paraffin. Since paraffin generally has a molecular weight distribution and has a wide range of boiling points, it is extremely difficult to separate paraffin by distillation operation.

The C6-C50 fluorine-free phenol may be a monovalent or polyvalent phenol compound. Examples of the C6-C50 fluorine-free phenols include phenol, di-t-butylphenol, cresol, naphthol, hydroquinone, catechol, resorcinol, pyrogallol, phloroglucinol, hexahydroxybenzene and the like.

The C1-C30 fluorine-free alcohol may be a monovalent or polyvalent alcohol compound. Examples of the C1-C30 fluorine-free alcohol include methanol, ethanol, propan-1-ol, butan-1-ol, pentan-1-ol, hexane-1-ol, heptan-1-ol, octan-1-ol, nonan-1-ol, decane-1-ol, undecan-1-ol, dodecan-1-ol, tridecan-1-ol, tetradecan-1-ol, pentadecan-1-ol, hexadecan-1-ol, heptadecan-1-ol, octadecan-1-ol, nonadecan-1-ol, icosan-1-ol, heneicosan-1-ol, docosan-1-ol, tricosan-1-ol, tetracosan-1-ol, pentacosan-1-ol, hexacosan-1-ol, heptacosan-1-ol, octacosan-1-ol, nonacosan-1-ol, triacontan-1-ol, policosanol, 2-methylpropan-1-ol, 3-methylbutan-1-ol, propan-2-ol, butan-2-ol, pentan-2-ol, hexane-2-ol, heptan-2-ol, 2-methylbutan-1-ol, cyclohexanol, 2-methylpropan-2-ol, 2-methylbutan-2-ol, 2-methylpentan-2-ol, 2-methylhexan-2-ol, 2-methylheptan-2-ol, 3-methylpentan-3-ol, 3-methyloctan-3-ol, ethylene glycol, glycerin, hydroquinone, catechol, 4-t-butyl catechol and the like.

Examples of the C8-C50 fluorine-free polyether include the followings:

a C8-C50 polyethylene glycol, a C8-C50 polypropylene glycol, a C8-C50 polyethylene/polypropylene glycol (herein, "polyethylene/polypropylene" means a group composed of an ethylene portion and a propylene portion), particularly a C8-C50 polyether polyol such as C8-C50 polyethylene glycol-polypropylene glycol-block ether;

a C8-C50 poly(oxyalkylene) alkyl ether such as a C8-C50 poly(oxyethylene) monoalkyl ether, a C8-C50 poly(oxyethylene) dialkyl ether, a C8-C50 poly(oxypropylene) monoalkyl ether, a C8-C50 poly(oxypropylene) dialkyl ether, a C8-C50 poly(oxyethylene)/(oxypropylene) monoalkyl ether, a C8-C50 poly(oxyethylene)/(oxypropylene) dialkyl ether (in the above, "(oxyethylene)/(oxypropylene)" means a group composed of an oxyethylene portion and an oxypropylene portion);

a C8-C50 poly(oxyalkylene) arylalkyl ether such as a C8-C50 poly(oxyethylene) monoaryl alkyl ether, a C8-C50 poly (oxyethylene) diaryl alkyl ether, a C8-C50 poly (oxypropylene) monoaryl alkyl ether, a C8-C50 poly (oxypropylene) diaryl alkyl ether, a C8-C50 poly (oxyethylene)/(oxypropylene) monoaryl alkyl ether, a C8-C50 poly (oxyethylene)/(oxypropylene) diarylalkyl ether (in the above, "(oxyethylene)/(oxypropylene)" means a group composed of an oxyethylene portion and an oxypropylene portion).

Examples of the C10-C20 fluorine-free alkyl group-containing ionic compound include the followings:

a C10-C20 alkyl sulfonate, for example, dodecyl sulfate and the like;

a C10-C20 alkylamine salt, for example, dodecylamine hydrochloride and the like;

a C10-C20 alkyl quaternary ammonium salt, for example, hexadecyl trimethyl ammonium bromide and the like;

a C10-C20 alkyl betaine, for example, dodecyl betaine and the like;

a C10-C20 alkylamine oxide salt, for example, dodecyldimethylamine oxide and the like.

However, the fluorine-free organic compound is not limited thereto, and it may be any other appropriate fluorine-free organic compound which can be added (and/or can be mixed), for example, as a dispersion stabilizer (a stabilizing aid), a surfactant, a chelating agent, a plasticizer, an initiator, a polymerization inhibitor, a chain transfer agent, an adhesion preventing agent, a machine oil and the like.

The content ratio of the fluorine-free organic compound in the mixture containing the C2-C20 fluorine-containing organic acid and the fluorine-free organic compound may be, for example, 1000 ppm by mass or less, particularly 500 ppm by mass or less, 200 ppm by mass or less, 100 ppm by mass or less, 50 ppm by mass or less, 30 ppm by mass or less, 20 ppm by mass or less, 10 ppm by mass or less, and but not particularly limited, it may be, for example, in the range of more than 0.1 ppm by mass. The content ratio of the fluorine-free organic compound in the above-mentioned mixture may be, for example, in the range of more than 0.1 ppm by mass to 100 ppm by mass, particularly in the range of 0.2 to 500 ppm by mass, 0.5 to 200 ppm by mass, 0.5 to 100 ppm by mass, 1 to 50 ppm by mass, 1 to 30 ppm by mass, 1 to 20 ppm by mass, 1 to 10 ppm by mass.

The mixture containing the C2-C20 fluorinated organic acid and the fluorine-free organic compound may contain other component which is, for example, a concentrated sulfuric acid, water, an inorganic substance (for example, an inorganic acids, a metal, other inorganic compound or elemental substance), divalent metal salt and the like. However, the content of water in the mixture containing the C2-C20 fluorine-containing organic acid and the fluorine-free organic compound is appropriately selected, according to the specific operation of the contact, so as to satisfy the condition relating to the amount of water in the contacting described later.

The mixture containing the C2-C20 fluorine-containing organic acid and the fluorine-free organic compound can be obtained by any suitable method, and, for example, it may be those derived from a reaction mixture after synthesizing the C2-C20 fluorine-containing organic acid or those derived from a reaction mixture after using the C2-C20 fluorine-containing organic acid for emulsion polymerization. Although not limiting to the present invention, for example, the mixture containing the C2-C20 fluorocarboxylic acid and the fluorine-free organic compound includes a reaction mixture obtained by a reaction (synthesis reaction) which produces the corresponding fluorocarboxylic acid by hydrolyzing the C2-C20 fluorocarboxylic acid fluoride, a reaction mixture obtained by a reaction (regeneration reaction) which produces the corresponding fluorocarboxylic acid by acidifying the C2-C20 fluorocarboxylic acid salt used in the emulsion polymerization, and the like. In the present specification, the term "derived" means that it may be obtained by appropriately subjecting the reaction mixture to post-treatment such as filtration, washing, deionization, dehydration, purification and the like.

The mixture containing the C2-C20 fluorine-containing organic acid and the fluorine-free organic compound may be previously subjected to dehydration treatment. By the dehydration treatment, the amount of water in the mixture can be reduced to a desired level (for example, to a substantially negligible level) so that it is possible to easily attain the condition relating to the amount of water in the contacting described later. The dehydration treatment may be carried out in either a batch manner or a continuous manner.

In one embodiment of the present invention, the dehydration treatment can be carried out by washing a mixture containing a precursor of the above-mentioned "the mixture containing the C2-C20 fluorine-containing organic acid and the fluorine-free organic compound" as well as water with a sulfuric acid aqueous solution having a sulfuric acid concentration of 70% by mass or more. The dehydration treatment can be carried out by, for example, contacting a mixture containing the C2-C20 fluorine-containing organic acid, the fluorine-free organic compound and water with a sulfuric acid aqueous solution having a sulfuric acid concentration of 70% by mass or more, for example 80% by mass or more, particularly 90% by mass or more, more particularly 96% by mass or more, further particularly 98% by mass or more, more further particularly 99.9% by mass or less, or typically a concentrated sulfuric acid, and then causing phase separation into a C2-C20 fluorine-containing organic acid phase (or an organic phase or a fluorous phase) and a sulfuric acid phase (it can be understood as an aqueous phase since water is more distributed to the sulfuric acid phase than the fluorine-containing organic acid phase) to obtain the above-mentioned "the mixture containing the C2-C20 fluorine-containing organic acid and the fluorine-free organic compound" in the form of the C2-C20 fluorine-containing organic acid phase. Herein, the sulfuric acid concentration means the sulfuric acid concentration of the sulfuric acid phase (the aqueous phase) during the dehydration treatment. The amount ratio of the mixture containing the C2-C20 fluorine-containing organic acid, the fluorine-free organic compound and water and the sulfuric acid aqueous solution is not particularly limited as long as the above sulfuric acid concentration can be maintained.

According to this embodiment, the mixture containing the C2-C20 fluorine-containing organic acid, the fluorine-free organic compound as well as water is subjected to contacting with a sulfuric acid aqueous solution (particularly a concentrated sulfuric acid) for the purpose of dehydration, and then is subjected to contacting with a concentrated sulfuric acid for the purpose of extraction (reduction or removal) of the fluorine-free organic compound, which will be described later. Therefore in summary, it will be washed at least twice with a sulfuric acid (especially a concentrated sulfuric acid). The contacting with a sulfuric acid 1C aqueous solution for the purpose of dehydration may be carried out twice or more until the desired dehydration (water content) level is reached. In this case, when it is summed with the contacting with a concentrated sulfuric acid for the purpose of extraction of the fluorine-free organic compound, schematically, it will be washed three or more times with sulfuric acid (especially concentrated sulfuric acid). The specific operation of the contacting with a sulfuric acid aqueous solution for the purpose of dehydration may be the same as the specific operation of the contacting with a concentrated sulfuric acid for the purpose of extraction (reduction or removal) of the fluorine-free organic compound, which is described later, except that what is phase separated from the C2-C20 fluorine-containing organic acid phase is not a concentrated sulfuric acid phase but a sulfuric acid phase (an aqueous phase). It should be noted that, when the C2-C20 fluorine-containing organic acid is in the form of a salt of the acid compound, it is acidified by contacting with a sulfuric acid or concentrated sulfuric acid to produce the corresponding acid compound.

However, the dehydration treatment is not limited to washing with a sulfuric acid, but any other appropriate method, for example, which is carried out by contacting the mixture containing the C2-C20 fluorine-containing organic acid, the fluorine-free organic compound and water with a water-absorbing substance such as diphosphorus pentaoxide, zeolite or the like (in the presence or absence of the above-mentioned sulfuric acid aqueous solution). Examples of zeolite include aluminosilicate and the like.

The water content of the mixture containing the C2-C20 fluorine-containing organic acid and the fluorine-free organic compound, which has been previously subjected to dehydration treatment, is, for example, 1.0% by mass or less, preferably 0.7% by mass or less, particularly preferably 0.2% by mass or less.

Then, in the method for producing the C2-C20 fluorinated organic acid of the present invention, in order to extract (reduce or eliminate) the fluorine-free organic compound, the mixture containing the C2-C20 fluorine-containing organic acid and the fluorine-free organic compound, as described above, is contacted with a concentrated sulfuric acid (hereinafter referred to as "extraction treatment of the fluorine-free organic compound").

In the present invention, "(a) concentrated sulfuric acid" refers to a sulfuric acid aqueous solution having a sulfuric acid concentration of 90% by mass or more. The sulfuric acid concentration of the concentrated sulfuric acid is, for example, 92% by mass or more, particularly 96% by mass or more, typically 98% by mass or more.

The mass ratio (the flow ratio in the case of continuous manner) of the mixture containing the C2-C20 fluorine-containing organic acid and the fluorine-free organic compound, and the concentrated sulfuric acid is not particularly limited as long as it can satisfy the condition relating to the amount of water in the contacting described later. However, it can be, for example, from 10:1 to 1:1, in particular from 10:2 to 10:5.

In the extraction treatment of the fluorine-free organic compound, it is preferable to stir and mix the mixture containing the C2-C20 fluorine-containing organic acid and the fluorine-free organic compound and the concentrated sulfuric acid so as to contact sufficiently with each other. For example, it is preferable to disperse the C2-C20 fluorine-containing organic acid phase in the concentrated sulfuric acid phase or to disperse the concentrated sulfuric acid phase in the C2-C20 fluorine-containing organic acid phase. More specifically, for example, droplets of the C2-C20 fluorine-containing organic acid phase can be dispersed as a dispersed phase in the concentrated sulfuric acid phase as a continuous phase. This promotes the contacting and the mass transfer between the concentrated sulfuric acid phase as the continuous phase and the C2-C20 fluorine-containing organic acid phase as the dispersed phase and therefore the fluorine-free organic compound can be effectively extracted from the C2-C20 fluorine-containing organic acid phase (or an organic phase or a fluorous phase) into the concentrated sulfuric acid phase. The dispersed phase and the continuous phase may be reversed. Thereafter, the mixture obtained by contacting them undergoes phase separation into the C2-C20 fluorine-containing organic acid phase and the concentrated sulfuric acid phase. The C2-C20 fluorine-containing organic acid and the concentrated sulfuric acid have low solubility with respect to each other and naturally phase-separate by substantially removing the stirring and mixing force. Then, the targeted C2-C20 fluorinated organic acid phase is separated and collected from the concentrated sulfuric acid phase.

The contacting of the mixture containing the C2-C20 fluorine-containing organic acid and the fluorine-free organic compound with the concentrated sulfuric acid in the extraction treatment of the fluorine-free organic compound is conducted such that the amount of water present in the concentrated sulfuric acid phase is 10% by mass or less. Thus, by containing the mixture containing the C2-C20 fluorine-containing organic acid and the fluorine-free organic compound with the concentrated sulfuric acid in a state in which substantially no water or a very small amount of water is present, the fluorine-free organic compound can be extracted from the C2-C20 fluorine-containing organic acid phase into the concentrated sulfuric acid phase (or at least partially removed from the C2-C20 fluorine-containing organic acid).

In the present invention, "the(an) amount of water present in the concentrated sulfuric acid phase" means the amount of water present in the concentrated sulfuric acid phase, before, during or after separating the C2-C20 fluorine-containing organic acid phase. The amount of water may be determined by calculation if possible (for example, wherein the concentrated sulfuric acid phase is considered to be substantially uniform irrespective of its part) or may be measured by directly analyzing the concentrated sulfuric acid phase sampled from any appropriate part of the apparatus performing the separation operation. Since the amount of water present in the concentrated sulfuric acid phase can be considered to be substantially the same from the contact interface between the C2-C20 fluorine-containing organic acid phase and the concentrated sulfuric acid phase to the outlet of the apparatus, the outlet concentration obtained by sampling the concentrated sulfuric acid phase withdrawn from the outlet of the apparatus and measuring its amount of water can be set as "the amount of water present in the concentrated sulfuric acid phase", without problems. The analysis can be carried out, for example, by Karl Fischer method. The amount of water may be 10% by mass or less, preferably 8% by mass or less, particularly 4% by mass or less, and more preferably 2% by mass or less.

As described above, the C2-C20 fluorine-containing organic acid can be obtained in the form of the C2-C20 fluorine-containing organic acid phase having the reduced content ratio of the fluorine-free organic compound as compared with the original mixture (mixture containing the C2-C20 fluorine-containing organic acid and the fluorine-free organic compound). It should be noted that the fluorine-free organic compound does not need to be extracted into the concentrated sulfuric acid phase as it is, and the fluorine-free organic compound may be reduced or removed in the C2-C20 fluorine-containing organic acid phase as compared with the original mixture. For example, the fluorine-free organic compound may be extracted in a state of being decomposed into the concentrated sulfuric acid phase.

The content ratio of the fluorine-free organic compound in the resulting C2-C20 fluorinated organic acid phase is preferably, for example, 0.1 ppm by mass or less, and particularly preferably 0.05 ppm by mass or less. The remainder of the C2-C20 fluorine-containing organic acid phase is preferably composed of the C2-C20 fluorinated organic acid.

In the present invention, the extraction treatment of the fluorine-free organic compound may be carried out in either a batch manner or a continuous manner. In the case of carrying out in a batch manner, the mixture containing the C2-C20 fluorine-containing organic acid and the fluorine-free organic compound is thoroughly mixed with the concentrated sulfuric acid, and then the mixed solution is left to stand (for example, mixing is stopped after mixing for a predetermined time) to phase-separate into the targeted C2-C20 fluorine-containing organic acid phase containing the C2-C20 fluorine-containing organic acid and the concentrated sulfuric acid phase and collect the C2-C20 fluorine-containing organic acid phase. If necessary, the resultant C2-C20 fluorine-containing organic acid phase can be again mixed with a concentrated sulfuric acid, and then the mixture can be left to stand to obtain the C2-C20 fluorine-containing organic acid phase having a smaller amount of the fluorine-free organic compound. This operation may be repeated until the concentration of the fluorine-free organic compound in the C2-C20 fluorine-containing organic acid phase becomes lower than the desired level.

Furthermore, the extraction treatment of the fluorine-free organic compound may include a step of continuously contacting a C2-C20 fluorine-containing acid phase and the concentrated sulfuric acid phase in a liquid-liquid heterophasic dispersion system consisting of the C2-C20 fluorine-containing organic acid phase and the concentrated sulfuric acid phase and a step of phase-separating the C2-C20 fluorinated organic acid phase and the concentrated sulfuric acid phase.

For example, referring to FIGS. 1 (a) and (b), it can be carried out as follows using a static mixer 10 and a liquid-liquid separation column 20. The mixture containing the C2-C20 fluorine-containing organic acid and the fluorine-free organic compound, and the concentrated sulfuric acid are supplied from any one and the other of supply ports 11 and 12 to the static mixer 10, respectively. The mixture containing the C2-C20 fluorine-containing organic acid and the fluorine-free organic compound, and the concentrated sulfuric acid are stirred and mixed by passing through the static mixer 10 in which an element 13 is installed, and the extraction of the fluorine-free organic compound can occur continuously in the static mixer 10. Thus mixed solution is discharged from a discharge port 14, and then supplied to the liquid-liquid separation column 20. The mixed solution supplied from the supply port 23 is liquid-liquid separated into a heavy liquid 21 and a light liquid 22 in the liquid-liquid separation column 20, and therefore the C2-C20 fluorine-containing organic acid phase can be collected. The correspondence relationship of the C2-C20 fluorine-containing organic acid phase and the concentrated sulfuric acid phase with the heavy liquid and the light liquid is determined depending on the densities (or the specific gravities) of the C2-C20 fluorine-containing organic acid phase and the concentrated sulfuric acid phase, and may vary depending on the type of the C2-C20 fluorine-containing organic acid. In such an embodiment, "the amount of water present in the concentrated sulfuric acid phase" is the amount of water present in the concentrated sulfuric acid phase withdrawn from the outlet of the liquid-liquid separation column 20. It may be measured by directly analyzing the concentrated sulfuric acid phase sampled from the outlet of the apparatus, or may be calculated from respective moisture contents of the mixture containing the C2-C20 fluorine-containing organic acid and the fluorine-free organic compound and of the concentrated sulfuric acid, which are supplied to the static mixer 10, assuming that all the water is present in the concentrated sulfuric acid phase in the liquid-liquid separation column 20.

Alternatively, the extraction treatment of the fluorine-free organic compound may be carried out continuously by using a contact type column so that the mixture containing the C2-C20 fluorine-containing organic acid and the fluorine-free organic compound, and the concentrated sulfuric acid are supplied so as to flow countercurrently. More specifically, the extraction of the fluorine-free organic compound may be carried out using a differential contact type extraction apparatus, which is a so-called "extraction column (tower)" (for example, a Karr column type extraction tower or the like), by supplying one as a light liquid (i.e., lower density) and the other as a heavy liquid (i.e., higher density) from the mixture containing the C2-C20 fluorine-containing organic acid and the fluorine-free organic compound, and the concentrated sulfuric acid, and contacting the two liquids in countercurrent.

Figure 2:
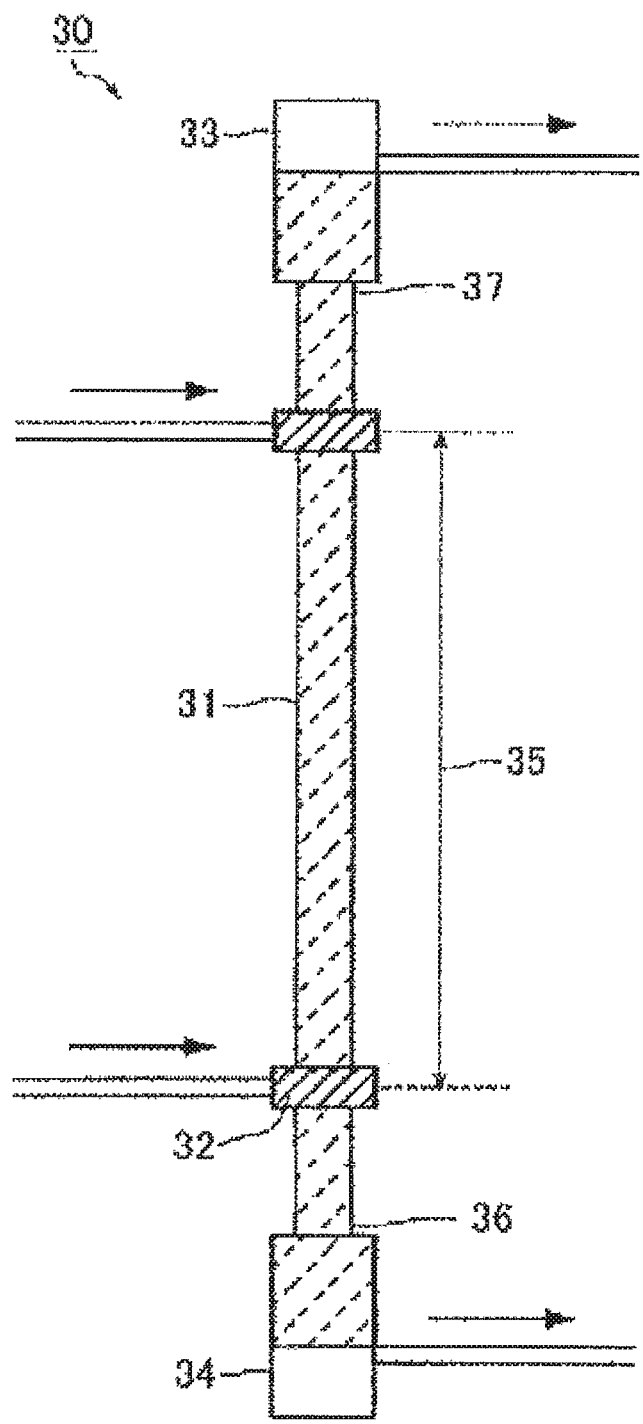
FIG. 2 is a schematic sectional view showing a configuration of a Karr column.

For example, referring to FIG. 2, it can be carried out as follows using a Karr column 30. One of the mixture containing the C2-C20 fluorine-containing organic acid and the fluorine-free organic compound, and the concentrated sulfuric acid is supplied as a heavy liquid to the upper portion of a cylindrical part 31 of the Karr column 30 and the other of those is supplied as a light liquid to the lower portion of the cylindrical part 31 (from a supply port 32) of the Karr column 30. The mixture containing the C2-C20 fluorine-containing organic acid and the fluorine-free organic compound, and the concentrated sulfuric acid are stirred and mixed by passing countercurrently through the cylindrical part 31 in which a stirring disk (not shown) is installed, thereby the extraction of the fluorine-free organic compound can occur continuously in the Karr column 30, particularly in an extraction zone 35. Thus mixed liquid forms the C2-C20 fluorine-containing organic acid phase and the concentrated sulfuric acid phase, and for example, liquid droplets of the C2-C20 fluorine-containing organic acid phase can be dispersed as a dispersed phase in the concentrated sulfuric acid phase as a continuous phase, and vice versa. The C2-C20 fluorine-containing organic acid phase and the concentrated sulfuric acid phase are caused by phase separation, the light liquid is collected from a tank part 33 connected to an upper end 37 of a cylindrical part, and the heavy liquid is collected from a tank part 34 connected to a lower end 36 of a cylindrical part. The correspondence relationship of the C2-C20 fluorine-containing organic acid phase and the concentrated sulfuric acid phase with the heavy liquid and the light liquid is determined depending on the densities (or the specific gravities) of the C2-C20 fluorine-containing organic acid phase and the concentrated sulfuric acid phase, and may vary depending on the type of the C2-C20 fluorine-containing organic acid. In such an embodiment, "the amount of water present in the concentrated sulfuric acid phase" is, in the case where the C2-C20 fluorine-containing organic acid phase is the light liquid, the amount of water present in the concentrated sulfuric acid phase (heavy liquid) taken out from the outlet of the tank part 34, and thus it can be measured by directly analyzing the concentrated sulfuric acid phase sampled from the outlet of the tank part 34. On the other hand, it is, in the case where the C2-C20 fluorine-containing organic acid phase is the heavy liquid, the amount of water present in the concentrated sulfuric acid phase (light liquid) taken out from the outlet of the tank part 33, and thus it can be measured by directly analyzing the concentrated sulfuric acid phase sampled from the outlet of the tank part 33.

As described above, the extraction treatment of the fluorine-free organic compound is carried out. Thus obtained C2-C20 fluorine-containing organic acid phase is characterized in that, since the fluorine-free organic compound is at least partially removed compared to the original mixture (the mixture containing the C2-C20 fluorine-containing organic acid and the fluorine-free organic compound), the content ratio of the fluorine-free organic compound is reduced and the purity of the C2-C20 fluorine-containing organic acid is improved. Therefore, the method for producing the C2-C20 fluorine-containing organic acid of the present invention can be understood as a method for treating the mixture containing the C2-C20 fluorine-containing organic acid and the fluorine-free organic compound so as to at least partially remove the fluorine-free organic compound, or as a method for purifying a C2-C20 fluorine-containing organic acid.

Since this extraction treatment of the fluorine-free organic compound can be carried out by contacting the mixture containing the C2-C20 fluorine-containing organic acid and the fluorine-free organic compound with the concentrated sulfuric acid and then causing phase separation, this can be carried out conveniently compared to the conventional operation such as distillation which is carried out as a method for purifying a C2-C20 fluorine-containing organic acid. In addition, the C2-C20 fluorine-containing organic acid phase obtained by the present invention may be further subjected to distillation. In this case, since the fluorine-free organic compound has reduced, it is possible to reduce the load on distillation.

On the other hand, the concentrated sulfuric acid phase generated in the extraction treatment of the fluorine-free organic compound may be collected separately and used for any suitable use. For example, the concentrated sulfuric acid phase, which is collected as such, may be recycled to the washing step with the sulfuric acid aqueous solution in the above dehydration treatment (for example in the next batch or in continuous manner). When the dehydration treatment and/or the extraction treatment is carried out twice or more, the concentrated sulfuric acid and/or the sulfuric acid used and collected in the latter step may be recycled to the preceding step, whereby, since the amount of the concentrated sulfuric acid and/or the sulfuric acid to be used can be reduced while efficiently extracting (reducing or removing) the fluorine-free organic compound, the reduction of cost can be achieved.

Although not intended to limit the present invention, the C2-C20 fluorine-containing organic acid obtained in the form of the C2-C20 fluorine-containing organic acid phase according to the present invention, if necessary after being subjected to post-treatment, can be used as an emulsifier when producing polymer by emulsion polymerization. In this case, since the fluorine-free organic compound is reduced and the purity of the C2-C20 fluorine-containing organic acid is improved, polymerization rate can be increased. Therefore, the method for producing the C2-C20 fluorine-containing organic acid of the present invention can be understood as a method for producing or purifying an emulsifier containing the C2-C20 fluorine-containing organic acid as a main component. In the present invention, when a reaction mixture after using the C2-C20 fluorine-containing organic acid for emulsion polymerization is used as the mixture containing the C2-C20 fluorine-containing organic acid and the fluorine-free organic compound, the method for producing the C2-C20 fluorine-containing organic acid according to the present invention can be understood as a method for regenerating the C2-C20 fluorine-containing organic acid (or an emulsifier containing the C2-C20 fluorine-containing organic acid as a main component). The main component of the emulsifier refers to a component functioning as an emulsifier, which means a component occupying 50% by mass or more, for example, 70% by mass or more, particularly 90% by mass or more, of the emulsifier.

It is desirable that the fluorine-free organic compound is completely removed in the C2-C20 fluorine-containing organic acid phase obtained by the method for producing the C2-C20 fluorine-containing organic acid of the present invention, but a composition containing the C2-C20 fluorine-containing organic acid and the fluorine-free organic compound is acceptable.

According to the present invention, it can be obtained a composition comprising a C2-C20 fluorine-containing organic acid and a fluorine-free organic compound, wherein a content ratio of the fluorine-free organic compound in the composition is 0.001 to 0.1 ppm by mass. The C2-C20 fluorine-containing organic acid and the fluorine-containing organic compound can be the same as described above. The content ratio of water in this composition may be, for example, 0.1% by mass or less, and particularly 0.05% by mass or less. The remainder of the composition can be substantially composed of the C2-C20 fluorine-containing organic acid and the purity of the C2-C20 fluorine-containing organic acid can be the upper limit of measurement accuracy, for example, 99.9% by mass or more. Such a composition can be obtained by the above-mentioned method for producing the C2-C20 fluorine-containing organic acid of the present invention, but is not limited thereto.

Although not intended to limit the present invention, the composition of the present invention, if necessary after being subjected to post-treatment, can be used as the C2-C20 fluorine-containing organic acid when producing a polymer by emulsion polymerization. In this case, since only a low level of fluorine-free organic compound is contained, it is possible to obtain a sufficiently high polymerization rate.

EXAMPLES

Hereinafter, the present invention will be described with examples. The concentration measurements in the following Examples and Comparative Examples were as follows.

The concentration of paraffin among the fluorine-free organic compound in the fluorine-containing organic acid phase was measured by gas chromatographic analysis. The analysis conditions used for the gas chromatographic analysis were as follows.
Detector: FID
Sample injection amount: 1 μL
Split ratio: 1/20
The concentrations of carboxylic acid compounds (more specifically succinic acid, oxalic acid, citric acid) among the fluorine-free organic compound in the fluorine-containing organic acid phase were measured by HPLC analysis.
The concentration of water was measured by Karl Fischer method.
The sulfuric acid concentration was measured by ion chromatography analysis.

Production Example 1

50 g of concentrated sulfuric acid having a concentration of 90% by mass (water of 10% by mass) was added to 100 g of a solution containing paraffin (a mixture of C20-C40 saturated hydrocarbons, the same shall apply hereinafter) as the fluorine-free organic compound in $CF_3OCF(CF_3)CF_2OCF(CF_3)$ COOH as the fluorine-containing organic acid (paraffin concentration in the whole of the solution: 25 ppm by mass), and then the fluorine-containing organic acid phase was taken out from the mixture to obtain a fluorine-containing organic acid solution 1. With respect to the fluorine-containing organic acid solution 1 obtained by this way, the concentration of paraffin as the fluorine-free organic compound was measured as 7.2 ppm by mass, and the concentration of water was 200 ppm by mass, and the concentration of sulfuric acid was 1200 ppm by mass.

Example 1

50 g of concentrated sulfuric acid having a concentration of 90% by mass (water of 10% by mass) was added to 100 g of the fluorine-containing organic acid solution 1 (paraffin concentration: 7.2 ppm by mass) prepared in Production Example 1, and then the fluorine-containing organic acid phase was taken out from the mixture. With respect to the fluorine-containing organic acid phase obtained by this way, the concentration of paraffin as the fluorine-free organic compound was measured. The result is shown in Table 1.

Example 2

50 g of concentrated sulfuric acid having a concentration of 92% by mass (water of 8% by mass) was added to 100 g of the fluorine-containing organic acid solution 1 (paraffin concentration: 7.2 ppm by mass) prepared in Production Example 1, and then the fluorine-containing organic acid phase was taken out from the mixture. With respect to the fluorine-containing organic acid phase obtained by this way, the concentration of paraffin as the fluorine-free organic compound was measured. The result is shown in Table 1.

Example 3

50 g of concentrated sulfuric acid having a concentration of 94% by mass (water of 6% by mass) was added to 100 g of the fluorine-containing organic acid solution 1 (paraffin concentration: 7.2 ppm by mass) prepared in Production Example 1, and then the fluorine-containing organic acid phase was taken out from the mixture. With respect to the fluorine-containing organic acid phase obtained by this way, the concentration of paraffin as the fluorine-free organic compound was measured. The result is shown in Table 1.

Example 4

50 g of concentrated sulfuric acid having a concentration of 96% by mass (water of 4% by mass) was added to 100 g of the fluorine-containing organic acid solution 1 (paraffin concentration: 7.2 ppm by mass) prepared in Production Example 1, and then the fluorine-containing organic acid phase was taken out from the mixture. With respect to the fluorine-containing organic acid phase obtained by this way, the concentration of paraffin as the fluorine-free organic compound was measured. The result is shown in Table 1.

Example 5

50 g of concentrated sulfuric acid having a concentration of 98% by mass (water of 2% by mass) was added to 100 g of the fluorine-containing organic acid solution 1 (paraffin concentration: 7.2 ppm by mass) prepared in Production Example 1, and then the fluorine-containing organic acid phase was taken out from the mixture. With respect to the fluorine-containing organic acid phase obtained by this way, the concentration of paraffin as the fluorine-free organic compound was measured. The result is shown in Table 1.

Production Example 2

50 g of concentrated sulfuric acid having a concentration of 90% by mass (water of 10% by mass) was added to 100 g of a solution containing succinic acid as the fluorine-free organic compound in $CF_3OCF(CF_3)CF_2OCF(CF_3)COOH$ as the fluorine-containing organic acid (succinic acid concentration in the whole of the solution: 25 ppm by mass), and then the fluorine-containing organic acid phase was taken out from the mixture to obtain a fluorine-containing organic acid solution 2. With respect to the fluorine-containing organic acid solution 2 obtained by this way, the concentration of succinic acid as the fluorine-free organic compound was measured as 4.3 ppm by mass, and the concentration of water was 200 ppm by mass, and the concentration of sulfuric acid was 1200 ppm by mass.

Example 6

50 g of concentrated sulfuric acid having a concentration of 98% by mass (water of 2% by mass) was added to 100 g of the fluorine-containing organic acid solution 2 (succinic acid concentration: 4.3 ppm by mass) prepared in Production Example 2, and then the fluorine-containing organic acid phase was taken out from the mixture. With respect to the fluorine-containing organic acid phase obtained by this way, the concentration of succinic acid as the fluorine-free organic compound was measured. The result is shown in Table 1.

Production Example 3

50 g of concentrated sulfuric acid having a concentration of 90% by mass (water of 10% by mass) was added to 100 g of a solution containing oxalic acid as the fluorine-free organic compound in $CF_3OCF(CF_3)CF_2OCF(CF_3)COOH$ as the fluorine-containing organic acid (oxalic acid concentration in the whole of the solution: 25 ppm by mass), and then the fluorine-containing organic acid phase was taken out from the mixture to obtain a fluorine-containing organic acid solution 3. With respect to the fluorine-containing organic acid solution 3 obtained by this way, the concentration of oxalic acid as the fluorine-free organic compound was measured as 2.8 ppm by mass, and the concentration of water was 200 ppm by mass, and the concentration of sulfuric acid was 1200 ppm by mass.

Example 7

50 g of concentrated sulfuric acid having a concentration of 98% by mass (water of 2% by mass) was added to 100 g of the fluorine-containing organic acid solution 3 (oxalic acid concentration: 2.8 ppm by mass) prepared in Production Example 3, and then the fluorine-containing organic acid phase was taken out from the mixture. With respect to the fluorine-containing organic acid phase obtained by this way, the concentration of oxalic acid as the fluorine-free organic compound was measured. The result is shown in Table 1.

Production Example 4

50 g of concentrated sulfuric acid having a concentration of 90% by mass (water of 10% by mass) was added to 100 g of a solution containing citric acid as the fluorine-free organic compound in $CF_3OCF(CF_3)CF_2OCF(CF_3)COOH$ as the fluorine-containing organic acid (citric acid concentration in the whole of the solution: 25 ppm by mass), and then the fluorine-containing organic acid phase was taken out from the mixture to obtain a fluorine-containing organic acid solution 4. With respect to the fluorine-containing organic acid solution 4 obtained by this way, the concentration of citric acid as the fluorine-free organic compound was measured as 9.8 ppm by mass, and the concentration of water was 200 ppm by mass, and the concentration of sulfuric acid was 1200 ppm by mass.

Example 8

50 g of concentrated sulfuric acid having a concentration of 98% by mass (water of 2% by mass) was added to 100 g of the fluorine-containing organic acid solution 4 (citric acid concentration: 9.8 ppm by mass) prepared in Production Example 4, and then the fluorine-containing organic acid phase was taken out from the mixture. With respect to the fluorine-containing organic acid phase obtained by this way, the concentration of citric acid as the fluorine-free organic compound was measured. The result is shown in Table 1.

TABLE 1

| | Fluorine-free organic compound | Concentrated sulfuric acid phase (% by mass) | | Concentration of Fluorine-free organic compound (ppm by mass) |
|---|---|---|---|---|
| | | Sulfuric acid | Water | |
| Example 1 | paraffin | 90 | 10 | 0.9 |
| Example 2 | paraffin | 92 | 8 | 0.09 |
| Example 3 | paraffin | 94 | 6 | 0.06 |
| Example 4 | paraffin | 96 | 4 | 0.02 |
| Example 5 | paraffin | 98 | 2 | 0.01 or less |
| Example 6 | succinic acid | 98 | 2 | 0.1 or less |
| Example 7 | oxalic acid | 98 | 2 | 0.1 or less |
| Example 8 | citric acid | 98 | 2 | 0.1 or less |

Production Example 5

50 g of concentrated sulfuric acid having a concentration of 90% by mass (water of 10% by mass) was added to 100 g of a solution containing paraffin (a mixture of C20-C40 saturated hydrocarbons, the same shall apply hereinafter) as the fluorine-free organic compound in $C_5F_{11}COOH$ as the fluorine-containing organic acid (paraffin concentration in the whole of the solution: 25 ppm by mass), and then the fluorine-containing organic acid phase was taken out from the mixture to obtain a fluorine-containing organic acid solution 5. With respect to the fluorine-containing organic acid solution 5 obtained by this way, the concentration of paraffin as the fluorine-free organic compound was measured as 5.5 ppm by mass, and the concentration of water was 450 ppm by mass, and the concentration of sulfuric acid was 4000 ppm by mass.

Example 9

50 g of concentrated sulfuric acid having a concentration of 98% by mass (water of 2% by mass) was added to 100 g of the fluorine-containing organic acid solution 5 (paraffin concentration: 5.5 ppm by mass) prepared in Production Example 5, and then the fluorine-containing organic acid phase was taken out from the mixture. With respect to the fluorine-containing organic acid phase obtained by this way, the concentration of paraffin as the fluorine-free organic compound was measured. The result is shown in Table 2.

Production Example 6

50 g of concentrated sulfuric acid having a concentration of 90% by mass (water of 10% by mass) was added to 100 g of a solution containing paraffin (a mixture of C20-C40 saturated hydrocarbons, the same shall apply hereinafter) as the fluorine-free organic compound in $C_3F_7OCF(CF_3)COO$ as the fluorine-containing organic acid (paraffin concentration in the whole of the solution: 25 ppm by mass), and then the fluorine-containing organic acid phase was taken out from the mixture to obtain a fluorine-containing organic acid solution 6. With respect to the fluorine-containing organic acid solution 6 obtained by this way, the concentration of paraffin as the fluorine-free organic compound was measured as 6.3 ppm by mass, and the concentration of water was 900 ppm by mass, and the concentration of sulfuric acid was 3200 ppm by mass.

Example 10

50 g of concentrated sulfuric acid having a concentration of 98% by mass (water of 2% by mass) was added to 100 g of the fluorine-containing organic acid solution 6 (paraffin concentration: 6.3 ppm by mass) prepared in Production Example 6, and then the fluorine-containing organic acid phase was taken out from the mixture. With respect to the fluorine-containing organic acid phase obtained by this way, the concentration of paraffin as the fluorine-free organic compound was measured. The result is shown in Table 2.

Production Example 7

50 g of concentrated sulfuric acid having a concentration of 90% by mass (water of 10% by mass) was added to 100 g of a solution containing paraffin (a mixture of C20-C40 saturated hydrocarbons, the same shall apply hereinafter) as the fluorine-free organic compound in $C_3F_7OCF(CF_3)$ $CF_2OCF(CF_3)COOH$ as the fluorine-containing organic acid (paraffin concentration in the whole of the solution: 25 ppm by mass), and then the fluorine-containing organic acid phase was taken out from the mixture to obtain a fluorine-containing organic acid solution 7. With respect to the fluorine-containing organic acid solution 7 obtained by this way, the concentration of paraffin as the fluorine-free organic compound was measured as 11.2 ppm by mass, and the concentration of water was 250 ppm by mass, and the concentration of sulfuric acid was 1600 ppm by mass.

Example 11

50 g of concentrated sulfuric acid having a concentration of 98% by mass (water of 2% by mass) was added to 100 g of the fluorine-containing organic acid solution 7 (paraffin concentration: 11.2 ppm by mass) prepared in Production Example 7, and then the fluorine-containing organic acid phase was taken out from the mixture. With respect to the fluorine-containing organic acid phase obtained by this way, the concentration of paraffin as the fluorine-free organic compound was measured. The result is shown in Table 2.

TABLE 2

| Fluorine-free organic compound | Concentrated sulfuric acid phase (% by mass) | | Concentration of Fluorine-free organic compound (ppm by mass) |
|---|---|---|---|
| | Sulfuric acid | Water | |
| Example 9 | paraffin | 98 | 2 | 0.01 or less |
| Example 10 | paraffin | 98 | 2 | 0.01 or less |
| Example 11 | paraffin | 98 | 2 | 0.01 or less |

Example 12

Figure 1B:
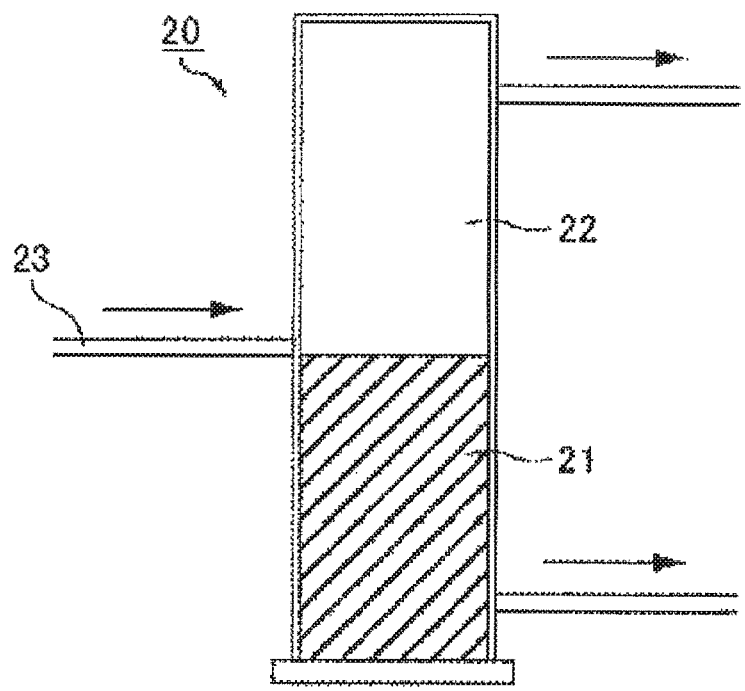

1000 g of the fluorine-containing organic acid solution 1' (paraffin concentration of 7.0 ppm by mass) prepared in the same manner as in Production Example 1 was passed from the supply port 11 of FIG. 1 (a) and 500 g of a concentrated sulfuric acid having a concentration of 90% by mass (10% by mass of water) was passed from the supply port 12 of FIG. 1 (a), and these were mixed by the static mixer 10. Thus mixed solution of them was discharged from the discharge port 14 of FIG. 1 (a), and then supplied to the liquid-liquid separation column 20. The mixed liquid supplied from the supply port 23 was left to stand and separated in the liquid-liquid separation column 20, and the fluorine-containing organic acid phase was taken out from the light liquid 22. With respect to the fluorine-containing organic acid phase obtained by this way, the concentration of paraffin was measured as 0.01 ppm by mass or less.

INDUSTRIAL APPLICABILITY

A method for producing a C2-C20 fluorine-containing organic acid of the present invention can be suitably used as a method for producing a C2-C20 fluorine-containing organic acid, in particular fluorocarboxylic acid, in which the fluorine-free organic compound is reduced.

This application claims priority based on Japanese Patent Application No. 2016-119807 filed on Jun. 16, 2016, the entire contents of which are hereby incorporated by reference.

REFERENCE SIGNS LIST 10 static mixer
11, 12, 23, 32 supply port
13 element
14 discharge port
20 liquid-liquid separation column
21 heavy liquid
22 light liquid
30 Karr column
31 cylindrical part
33, 34 tank part
35 extraction zone
36 lower end of cylindrical part
37 upper end of cylindrical part

The invention claimed is:
1. A method for producing a $C_2$-$C_{20}$ fluorine-containing organic acid, wherein the method comprises:
   contacting a mixture containing a $C_2$-$C_{20}$ fluorine-containing organic acid and a fluorine-free organic compound with a concentrated sulfuric acid and then separating a $C_2$-$C_{20}$ fluorine-containing organic acid phase from a concentrated sulfuric acid phase,
   wherein the contacting is conducted such that the amount of water present in the concentrated sulfuric acid phase is 10% by mass or less and the amount of a sulfuric acid in the concentrated sulfuric acid phase is 90% by mass or more,
   the $C_2$-$C_{20}$ fluorine-containing organic acid is obtained in the form of the $C_2$-$C_{20}$ fluorinated organic acid phase,
   a content of the fluorine-free organic compound in the $C_2$-$C_{20}$ fluorinated organic acid phase is less than a content of the fluorine-free organic compound in the mixture,
   the $C_2$-$C_{20}$ fluorine-containing organic acid comprises at least one selected from the group consisting of a $C_2$-$C_{20}$ fluorocarboxylic acid and salts thereof, and
   the fluorine-free organic compound comprises at least one selected from the group consisting of a $C_1$-$C_{50}$ fluorine-free carboxylic acid and derivatives thereof, a $C_8$-$C_{50}$ fluorine-free hydrocarbon, a $C_6$-$C_{50}$ fluorine-free phenol, a $C_1$-$C_{30}$ fluorine-free alcohol, a $C_8$-$C_{50}$ fluorine-free polyether, and a $C_{10}$-$C_{20}$ fluorine-free alkyl group-containing ionic compound.

2. The method according to claim 1, wherein the fluorine-free organic compound comprises a $C_1$-$C_{50}$ fluorine-free carboxylic acid.

3. The method according to claim 1, wherein the fluorine-free organic compound comprises the $C_8$-$C_{50}$ fluorine-free hydrocarbon.

4. The method according to claim 1, wherein, prior to the contacting, the mixture containing the $C_2$-$C_{20}$ fluorine-containing organic acid and the fluorine-free organic compound is subjected to a dehydration treatment.

5. The method according to claim 4, wherein the dehydration treatment is carried out by washing the mixture containing the $C_2$-$C_{20}$ fluorine-containing organic acid and the fluorine-free organic compound with a sulfuric acid aqueous solution having a sulfuric acid concentration of 70% by mass or more.

6. The method of claim 1, wherein a ratio by mass of the mixture to the concentrated sulfuric acid is 10:1 to 1:1.

7. The method of claim 1, wherein a content of the fluorine-free organic compound in the mixture is 0.1 ppm by mass to 1000 ppm by mass.

8. The method according to claim 1, wherein the $C_2$-$C_{20}$ fluorocarboxylic acid is represented by the following formula (i):

$$X-R_f-COOH \quad \text{formula (i)},$$

wherein, in the formula (i), X is H, F or Cl, Rf is a linear or branched $C_1$-$C_{19}$ fluoroalkylene group, a $C_1$-$C_{19}$ group having a monooxyfluoroalkylene group or a $C_1$-$C_{19}$ group having a polyoxyfluoroalkylene group.

9. The method according to claim 8, wherein Rf is represented by one of the following formula (a) to (f):

$(CF_2)_l$—$(CF_2OCF_2)_m$—$(CF_2OCF(CF_3))_n$  formula (a), $(CF_2)_l$—$(CHFOCF_2)_m$—$(CF_2OCF(CF_3))_n$  formula (b), $(CF_2)_l$—$(CF_2OCHF)_m$—$(CF_2OCF(CF_3))_n$  formula (c), $(CHF)_l$—$(CF_2OCF_2)_m$—$(CF_2OCF(CF_3))_n$  formula (d), $(CHF)_l$—$(CHFOCF_2)_m$—$(CF_2OCF(CF_3))_n$  formula (e), $(CHF)_l$—$(CF_2OCHF)_m$—$(CF_2OCF(CF_3))_n$  formula (f), wherein, in the formula (a) to (f), l is 0 or an integer of 1 to 17, m is 0 or an integer of 1 to 9 and n is an integer of 0 to 6, provided that l+2m+3n does not exceed 19 and that a case where m and n are 0 is excluded and that the order of presence of the respective repeating units in parentheses is arbitrary.

10. The method according to claim 8, wherein X is H or F, and Rf is represented by the following formula (a):

$(CF_2)_l$—$(CF_2OCF_2)_m$—$(CF_2OCF(CF_3))_n$  formula (a), wherein, in the formula (a), l is 0 or an integer of 1 to 17, m is 0 or an integer of 1 to 9 and n is an integer of 0 to 6, provided that l+2m+3n does not exceed 19, that a case where m and n are 0 is excluded, and that the order of presence of the respective repeating units in parentheses is arbitrary.

11. The method according to claim 1, wherein the $C_2$-$C_{20}$ fluorocarboxylic acid is selected from the group consisting of:

$CF_3OCF(CF_3)CF_2OCF(CF_3)COOH$,
$CF_3CF_2OCF_2CF_2OCF_2COOH$,
$CF_3OCF_2CF_2CF_2OCHFCF_2COOH$,
$CF_3CF_2OCF_2CF_2OCF_2COOH$,
$CF_3OCF_2CF_2CF_2OCHFCF_2COOH$,
$CF_3(CF_2)_4COOH$,
$CF_3CF_2CF_2OCF(C(CF_3)COOH$,
$H(CF_2)_6COOH$,
$H(CF_2)_4COOH$,
$CH_2=CFCF_2OCF(CF_3)COOH$,
$CF_3(CF_2)_6COOH$, and
$CF_3CFCF_2COCF_2CF_2OCF(CF_3)COOH$.

12. The method according to claim 1, wherein the fluorine-free organic compound comprises the $C_1$-$C_{50}$ fluorine-free carboxylic acid, and the $C_1$-$C_{50}$ fluorine-free carboxylic acid comprises a $C_8$-$C_{50}$ fluorine-free aromatic carboxylic acid or ester thereof.

13. The method according to claim 1, wherein the fluorine-free organic compound comprises the $C_1$-$C_{50}$ fluorine-free carboxylic acid, and the $C_1$-$C_{50}$ fluorine-free carboxylic acid comprises a $C_1$-$C_{50}$ fluorine-free aliphatic carboxylic acid or ester thereof.

14. The method according to claim 1, wherein the fluorine-free organic compound comprises the $C_8$-$C_{50}$ fluorine-free hydrocarbon, and the $C_8$-$C_{50}$ fluorine-free hydrocarbon comprises a $C_8$-$C_{50}$ linear, branched or alicyclic and saturated or unsaturated hydrocarbon.

15. The method according to claim 1, wherein the fluorine-free organic compound comprises a polyvalent $C_6$-$C_{50}$ fluorine-free phenol.

16. The method according to claim 1, wherein the fluorine-free organic compound comprises a polyvalent $C_1$-$C_{30}$ fluorine-free alcohol.

17. The method according to claim 1, wherein the fluorine-free organic compound comprises the $C_8$-$C_{50}$ fluorine-free polyether, and the $C_8$-$C_{50}$ fluorine-free polyether is selected from the group consisting of a $C_8$-$C_{50}$ polyethylene glycol, a $C_8$-$C_{50}$ polypropylene glycol, a $C_8$-$C_{50}$ polyethylene/polypropylene glycol, a $C_8$-$C_{50}$ poly(oxyalkylene)alkyl ether, and a $C_8$-$C_{50}$ poly(oxyalkylene)arylalkyl ether.

18. The method according to claim 1, wherein the fluorine-free organic compound comprises the $C_{10}$-$C_{20}$ fluorine-free alkyl group-containing ionic compound, and the $C_{10}$-$C_{20}$ fluorine-free alkyl group-containing ionic compound is selected from the group consisting of a $C_{10}$-$C_{20}$ alkyl sulfonate, a $C_{10}$-$C_{20}$ alkylamine salt, a $C_{10}$-$C_{20}$ alkyl quaternary ammonium salt, a $C_{10}$-$C_{20}$ alkyl betaine, and a $C_{10}$-$C_{20}$ alkylamine oxide salt.

19. The method according to claim 1, wherein a content of the fluorine-free organic compound in the $C_2$-$C_{20}$ fluorinated organic acid phase is less than 0.1 ppm by mass.

20. The method according to claim 1, wherein a content of the fluorine-free organic compound in the $C_2$-$C_{20}$ fluorinated organic acid phase is less than 0.05 ppm by mass.

* * * * *